United States Patent [19]
Gazzara et al.

[11] Patent Number: 5,743,270
[45] Date of Patent: Apr. 28, 1998

[54] RESISTIVE ELEMENT FOR SPIROMETER

[75] Inventors: Peter J. Gazzara, Reading; John W. Burke, Jr., Melrose, both of Mass.

[73] Assignee: Desert Moon Development Limited Partnership, Dana Point, Calif.

[21] Appl. No.: 667,396

[22] Filed: Jun. 21, 1996

[51] Int. Cl.$^6$ ........................................ A61B 5/08
[52] U.S. Cl. .................... 128/724; 128/725; 128/716; 73/861.54; 73/861.55
[58] Field of Search .................. 128/725, 724, 128/716, 720, 730; 73/861.52, 861.54, 861.55, 861.65

[56] References Cited

U.S. PATENT DOCUMENTS

| | | |
|---|---|---|
| D. 272,184 | 1/1984 | Karpowicz . |
| 3,232,288 | 2/1966 | Krobath .................... 128/724 |
| 4,122,842 | 10/1978 | Pikul . |
| 4,403,514 | 9/1983 | Osborn . |
| 4,640,293 | 2/1987 | Garbe . |
| 4,679,573 | 7/1987 | Parnoff et al. .................... 128/716 |
| 4,807,641 | 2/1989 | Boehringer et al. . |
| 4,852,583 | 8/1989 | Walker .................... 128/716 |
| 4,905,709 | 3/1990 | Bieganski et al. . |
| 4,989,456 | 2/1991 | Stupecky . |
| 4,995,400 | 2/1991 | Boehringer et al. . |
| 5,038,621 | 8/1991 | Stupecky . |
| 5,038,773 | 8/1991 | Norlien et al. . |
| 5,060,655 | 10/1991 | Rudolph . |
| 5,111,827 | 5/1992 | Rontala . |
| 5,137,026 | 8/1992 | Waterson et al. . |
| 5,277,195 | 1/1994 | Williams . |
| 5,277,196 | 1/1994 | Hankinson et al. . |
| 5,287,851 | 2/1994 | Beran et al. . |
| 5,288,318 | 2/1994 | Mayer et al. . |
| 5,292,782 | 3/1994 | Bastioli et al. . |
| 5,296,526 | 3/1994 | Delrue et al. . |
| 5,305,762 | 4/1994 | Acorn et al. . |
| 5,379,650 | 1/1995 | Koford et al. . |
| 5,564,432 | 10/1996 | Thomson .................... 73/861.52 |

OTHER PUBLICATIONS

Advance For Respiratory Managers (Aug. 1996).
Respiradyne®, Pulmonary Function/Ventilation Monitor Operation Manual (1990).
MultiSPIRO–SX Specifications (Date unknown).
DuPont Material Safety Data Sheet Nomex®, Aramid Fiber (Nov. 1993).

*Primary Examiner*—Jennifer Bahr
*Assistant Examiner*—Stephen Huang
*Attorney, Agent, or Firm*—Kenton R. Mullins; Frank J. Uxa

[57] ABSTRACT

The present air tubes include a resistive element which is located in the hollow space of the tubular portion. This resistive element is adapted for providing a linear resistance-versus-pressure response is sized and adapted to cause a pressure difference or differential as air flows in the hollow space across this element. The resistive element includes a planar member having a first face and a second face, and a circular parameter connecting the first face to the second face. An aperture is formed in a center of the planar member for connecting the first face to the second face. A plurality of slots in the planar member extend radially from the aperture, thereby forming a plurality of hinged windows in the planar member. Each of the slots includes a central end and a distal end. The resistive element further includes a plurality of hinge slots. Each hinge slot is connected to a distal end of a slot, and extends generally perpendicularly to an axis of the slot. A total number of hinge slots corresponds to a total number slots.

21 Claims, 4 Drawing Sheets

RESISTIVE ELEMENT FOR SPIROMETER

BACKGROUND OF THE INVENTION

The present invention relates to resistive elements for use with spirometers, and to spirometers using such resistive elements. More particularly, the present invention relates to air tubes and resistive elements which are disposable and to spirometers, preferably differential pressure spirometers, which employ such tubes and elements.

Spirometers are devices used to measure the volume and flow rate of gas exhaled and inhaled by a user or patient, for example, a human being. These measurements are important for physiological studies and for diagnostic analysis of the pulmonary performance of the spirometer user. For example, the effects of various medicines used to treat patients with pulmonary or asthmatic problems can be analyzed by monitoring the volume and flow rate of gas exhaled before and after the administration of medication. Several devices are available on the market which are known as pneumotachs, such as the Fleisch Pneumotach. These devices depend on a laminar air flow past a resistance element. Other spirometers employ more sophisticated electronics so that laminar flow is not needed.

Measuring the pressure difference or differential pressure of exhaled gas across an element which creates or causes the pressure difference is the basis for differential pressure spirometers. In such differential pressure spirometers, it is important that the air tube (pneumotach) be precisely configured and positioned, for example, relative to the pressure sensing and electronics systems of the spirometers so that measurements can be reliably and reproducibly made. Such precisely configured pneumotachs, rather than being disposable, are made out of metals or durable plastics to be long lasting and effective after many uses without structural degradation. See, for example, Waterson et al U.S. Pat. No. 5,137,026, the disclosure of which is hereby incorporated in its entirety by reference herein.

Since most spirometers involve passing exhaled gas directly from the respiratory system of a user into the instrument for measuring, one important complication of using such devices is contamination from one patient to another patient if the same spirometer is employed by both.

Various approaches to overcoming this contamination problem have been suggested. A particularly popular approach is to use a disposable mouthpiece and filter over the inlet to the spirometer. The patient using the spirometer comes in contact only with the mouthpiece and is able, at least in theory, to avoid contaminating the remainder of the device. Drawbacks to this approach include the relative expense of such mouthpieces/filters, and the relative inefficiency of such systems.

Another approach to overcoming this contamination problem is to sterilize the portion or portions of the spirometer which come in contact with the user and/or exhaled air. Drawbacks to this approach include having to spend additional capital on sterilization equipment, having to monitor the operation and efficacy of the sterilization equipment, and having to purchase relatively durable and expensive spirometers to withstand the sterilization procedures.

A third alternative that has been suggested is the use of disposable spirometer components. See, for example, Norlien et al U.S. Pat. No. 5,038,773; Acorn et al U.S. Pat. No. 5,305,762; Karpowicz U.S. Pat. Des. 272,184; Boehringer et al U.S. Pat. No. 4,807,641; and Bieganski et al U.S. Pat. No. 4,905,709.

Such previous disposable spirometer components have been made out of durable plastics or medical grade metals so that, even though they are disposable, the cost of producing such components is relatively high. In addition, such disposable components are relatively difficult to dispose of, for example, because they are made of durable and long lasting materials.

The placement of the resistive element within each air tube can affect the performance of the overall spirometer. The resistive element is often placed in a normal or perpendicular configuration relative to the interior wall of the air tube, at exact, predetermined distances from the two opposing ends of the air tube. Prior art resistive elements often do not exhibit linear resistance-versus-flow-rate responses. More particularly, resistive elements configured to exhibit good resistance at high air flow rates (at approximately atmospheric pressure) often do not perform adequately at low flow rates and, on the other hand, resistive elements configured to perform well at low flow rates often do not provide ideal resistance at high flow rates.

A typical resistive element for a spirometer includes a disk-shaped member with a large aperture through the center thereof. Other resistive elements of the prior art may include disk-shaped elements formed of a mesh material. Another prior art device includes a diamond-shaped window formed in a center portion of the disk shaped member. The diamond-shaped window is secured to a portion of the disk shaped element, and is adapted for opening and shutting to various extents or degrees, depending upon the air flow rate.

A prior art resistive element formed of a mesh is typically rendered inoperative or inaccurate by moisture and sputom from the patient's breath, resulting in clogging of the mesh. Prior art resistive elements comprising a diamond-shaped window have been somewhat effective for low air flow rates, but have not provided fully effective resistance-versus-pressure responses at both high and low flow rates.

It would be advantageous to provide spirometers and spirometer components which exhibit linear characteristics and which can be economically, conveniently and effectively produced and used.

SUMMARY OF THE INVENTION

New air tubes and resistive elements for use in spirometers and spirometers including such air tubes and resistive elements have been discovered. The present air tubes and resistive elements are disposable so that after use by a patient, they are removed from the spirometer and disposed. The air tubes and resistive elements are almost completely biodegradable.

As used herein, the term "biodegradable" means that the component or material is decomposable into more environmentally acceptable components, such as carbon dioxide, water, methane and the like, by natural biological processes, such as microbial action, for example, if exposed to typical landfill conditions, in no more than five years, preferably no more than three years, and still more preferably no more than one year.

Having the air tube and resistive elements biodegradable provides substantial advantages. First, when the air tube and resistive elements are disposed of, the burden on the environment of such disposal is reduced relative to, for example, a non-biodegradable air tube, such as those made out of conventional plastics or metals. In addition, because the air tube and resistive elements are biodegradable, they can be made of materials which are inexpensive and plentiful (readily available). Thus, the present air tubes and resistive elements are relatively inexpensive, easy and straightforward to produce, requiring little or no sophisticated production equipment. Since the present air tubes and resistive elements can be made economically, replacing a used air tube with a new air tube is done without substantial economic impact. In addition, the present air tubes and resistive elements can be replaced in the spirometer very easily. These advantages promote operator compliance in that the spirometer operator (for example, the care provider or the patient operating the spirometer) is more likely to change the present air tubes and resistive elements after each patient or treatment, thus reducing the risks of contamination and the spread of diseases, for example, tuberculosis and other respiratory system disorders, AIDS, other systemic conditions and the like.

Spirometers employing the present air tubes provide cost effective, reliable and reproducible (from air tube to air tube), measurements of the pulmonary performance of the user, with reduced risk of contamination. In short, the present disposable, biodegradable spirometer air tubes and resistive elements are inexpensive and easy to produce to acceptably precise specifications (for reproducible performance), are effective and reliable in use, and are conveniently and effectively disposed of in an environmentally acceptable or safe manner to reduce the risks of contamination caused by spirometer use.

In one broad aspect, the present invention is directed to air tubes for use in spirometers. The present air tubes comprise a tubular portion which defines an open inlet, an open, preferably opposing, outlet and a hollow space therebetween. The tubular portion is sized and adapted to be removably coupled to the housing of a spirometer. The air tube is disposable, i.e., can be removed or decoupled from the spirometer housing and disposed of without disposing of the housing. Substantially all of the tubular portion is preferably biodegradable. The open inlet is sized and adapted to be received in the mouth of the user of the spirometer. Thus, this open inlet and the area of the tubular portion near the open inlet act as a mouthpiece for the spirometer so that the user or patient using the spirometer can exhale into the air tube directly through the open inlet. No separate and/or specially configured (relatively expensive) mouthpiece/filter is needed when using the present air tubes.

The present air tubes include a resistive element which is located in the hollow space of the tubular portion. This resistive element is sized to cause a pressure difference or differential as air flows in the hollow space across this element, and is adapted for providing an alinear flow-versus-pressure response. This response is subsequently linearized with software. The resistive element includes a planar portion having a first face and a second face, and a parameter connecting the first face to the second face. An aperture is formed in a center of the planar portion for connecting the first face to the second face. A plurality of slots in the planar portion extend radially from the aperture, thereby forming a plurality of hinged windows in the planar portion. Each of the slots includes a central end and a distal end. The resistive element further includes a plurality of hinge slots. Each hinge slot is connected to a distal end of a slot, and extends generally perpendicularly to an axis of the slot. A total number of hinge slots corresponds to a total number slots.

According to one aspect of the present invention, the slots and hinge slots form arrowhead-shaped, hinged windows. Each hinged window includes a point, which points toward the center of the planar member, and a neck, which controls the flexibility of the window. A large neck reduces the flexibility of the hinged window, and a small neck increases the flexibility of the hinged window. The resistive element has an approximately linear pressure response over a range of flow rates from zero liters per second to 15 liters per second.

According to another aspect of the present invention, an air tube is formed of a first tube, a second tube, and a collar tube. The first tube has a proximal end, a distal end, and a first diameter. The second tube, similarly, has a proximal end, a distal end, and a second diameter that is approximately equal to the first diameter. A resistive element contacts the proximal end of the first tube and the distal end of the second tube, and has a third diameter that is approximately equal to the first diameter. A collar tube fits over both the proximal end of the first tube and the distal end of the second tube. The collar tube has an inner diameter that is approximately equal to the first diameter, and has an outer diameter that is larger than the first diameter. A through port is formed in the second tube. The through port opens directly into a hollow space defined by the tube assembly and is spaced from the resistive element. The through port provides communication between the hollow space of the tubular assembly and a pressure sensing assembly of a spirometer. The pressure sensing assembly of the spirometer compares a pressure from the hollow space with an atmospheric pressure.

The tubular portions and resistive elements of the present air tubes preferrably comprise biodegradable materials, and are more preferrably 99% biodegradable. Preferred biodegradable materials of construction include cardboard, paper, biodegradable polymeric materials and the like and mixtures thereof. In one particularly useful embodiment, the tubular portion is made of cardboard or paper or mixtures thereof, more preferably produced by methods analogous to those conventionally used to produce tubes around which are wound bathroom tissue. Such production methods often include forming a cardboard or paper tube over a mandrel or a like implement and then cutting the resulting tube to the desired length. In the event that the tubular portion is made from a biodegradable polymeric material such tubes can be formed by conventional polymer molding techniques.

The resistive element is placed relative to the tubular portion so that the pressure difference for any given rate of flow of air across the resistive element is the same from air tube to air tube. The resistive element is preferably located transverse to the longitudinal axis of the tubular portion. The resistive element can be placed in the tubular portion by adhering (for example, using biodegradable adhesives) the resistive element to the interior wall of the tubular portion or by joining two separate segments of the tubular portion together with the resistive element therebetween. Other methods or techniques for placing the resistive elements in the tubular portions may be employed. Preferably, the resistive elements of the present air tubes designed for use in the same spirometer are structured and configured essentially the same, so that no recalibration of or other adjustment to the spirometer is needed because one air tube is replaced by another air tube.

In a preferred embodiment, the present air tubes further comprise a positioning means or sub-system adapted to cooperate with the housing of the spirometer to properly position the air tube relative to the housing of the spirometer. Any suitable positioning means may be employed to properly orient the air tube relative to the housing of the spirometer, for example, so that the through port of the air tube is properly aligned with the pressure sensing assembly of the spirometer.

In one specific embodiment, the positioning means includes a notch sized and adapted to cooperate with a projection on the housing of the spirometer. In another specific embodiment, the positioning means includes a positioning port in the tubular portion sized and adapted to cooperate with a positioning projection in the housing of the spirometer. This is a particularly useful embodiment since the positioning port can be easily placed in the tubular portion of the air tube. Also, since the housing of the spirometer is often a molded polymeric component, the positioning projection can be easily formed in the spirometer housing.

An air tube in accordance with the present invention can be snugly fitted into a hollow open space defined by a spirometer housing tube so that the through port of the tubular portion is properly aligned with the pressure sensing assembly of the spirometer. To insure such proper alignment, the projections of the housing can be placed in the notch of the tubular portion such that the through port of the tubular portion is properly aligned with the pressure-sensing assembly of the spirometer.

A suction-cup shaped interface of the pressure sensing assembly fits snugly around the through port. The snugness of the fit between the air tube and the housing tube of the spirometer insures that the air tube can be used in conjunction with the spirometer without disturbing the through port/pressure sensing assembly alignment. After use, the air tube can be relatively easily removed from the spirometer housing tube and replaced by a new air tube.

The present air tubes can be designed and structured to be used with a retrofitted existing spirometer or with a spirometer specifically built for use with the air tubes. It is particularly useful to have the tubular portion longer than the housing of the spirometer so that in use the tubular portion extends beyond at least one end of the component of the housing of the spirometer to which the tubular portion is removably coupled. This feature is very attractive in preventing undue contamination of the spirometer housing by the user of the spirometer. Thus, the air which is exhaled by the patient passes through the tubular portion and does not come into significant or intimate contact with the housing of the spirometer.

In another broad aspect of the present invention, new spirometers are provided. The present spirometers comprise a housing, an air tube as described herein, a pressure sensing assembly positioned relative to a through ports of the air tube to sense the pressure at the through port, and an electronic assembly coupled to the pressure sensing assembly for generating signals, preferably electrical signals, indicative of the differential between the pressure sensed at the through port and an atmospheric pressure. The electronic assembly can be disposed in the housing or can be located remote from the housing. For example, the housing can be a hand held component which is connected, for example, by wire, cable, or an RF path, to an electronic processing system which includes a substantial portion of the electronic assembly of the present spirometer. Alternately, the electronic assembly can be completely disposed in the spirometer housing so that a fully self-contained unit can be provided.

Although many of the features of the present invention are described separately, more than one or all of such features can be used in various combinations, provided that such features are not mutually inconsistent, and all of such combinations are within the scope of the present invention. These and other aspects and advantages of the present invention are set forth in the following detailed description and claims, particularly when considered in conjunction with the accompanying drawings in which like parts bear like reference numerals.

DETAILED DESCRIPTION OF THE DRAWINGS

Figures 1, 1A:
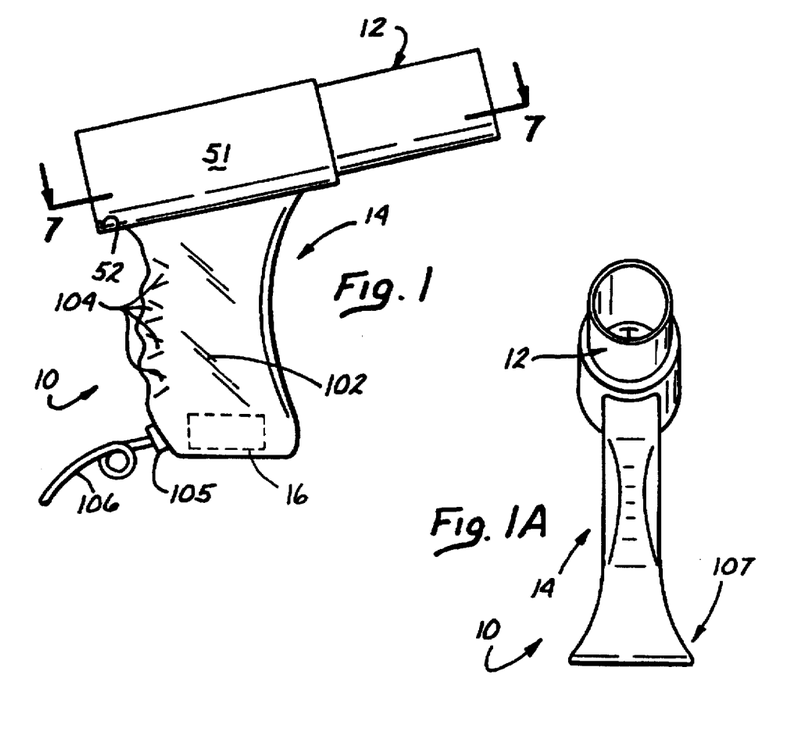
FIG. 1 is a side view of a spirometer in accordance with the present invention showing a portion of the electronics disposed apart from the hand held unit.
FIG. 1A is a front side view of the spirometer shown in FIG. 1.

Referring to FIGS. 1 and 1A, a spirometer in accordance with the present invention, shown generally at 10, includes a disposable, biodegradable air tube 12, a housing 14 and control electronics 16. Spirometer 10 is what is commonly known as a differential pressure spirometer and, in general, operates in a manner similar to the spirometer disclosed in the above-noted Waterson et al U.S. Pat. No. 5,137,026.

Figure 2:
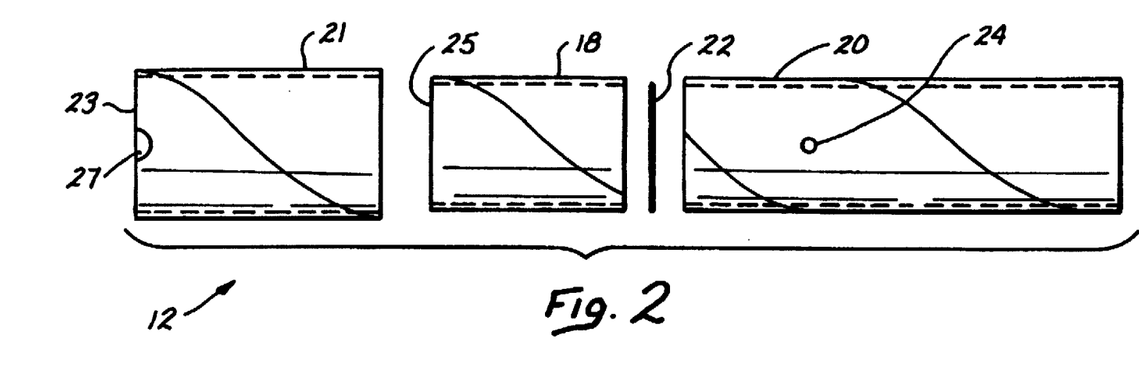
FIG. 2 is an exploded view of the air tube of the presently preferred embodiment.

The air tube 12 is described with reference to FIGS. 2 and 3. The air tube 12 includes a first tubular segment 18, a second tubular segment 20, and a collar tube 21. A resistive element 22 fits between the first tubular segment 18 and the second tubular segment 20. The air tube 12 and resistive element 22 are preferably approximately ninety-nine percent biodegradable. The tubular segments 18, 20, and 21 are made of biodegradable cardboard or heavy paper, for example, in a manner similar to how cardboard tubes are conventionally made, such as for use with bathroom tissue and the like products. These segments 18, 20, and 21 are preferably coated with a thin glossy layer. The resistive element 22 preferably comprises biodegradable material having good memory characteristics. As presently embodied, the resistive element 22 comprises a Nomex material. The resistive element 22 material may, alternatively, comprise any nylon or other material which is somewhat resistant to moisture. As presently embodied, the resistive element 22 is approximately 0.003 inches thick, but other thicknesses may be used according to design parameters.

The resistive element 22 is first secured to either the first tubular segment 18 or the second tubular segment 20, and then the other tubular segment 18 or 20 is then secured to the resistive element 22. A biodegradable adhesive is preferably used. As presently embodied, an outer diameter of the first tubular segment 18 is equal to an outer diameter of the second tubular segment 20, and the outer diameter of the resistive element 22 is equal to the outer diameter of the first tubular segment 18.

An inner diameter of the collar tube 21 is approximately equal to the outer diameter of the first tubular segment 18. The collar tube 21 is adapted to fit over both the first tubular segment 18 and the second tubular segment 20. Although adhesives are preferably used for securing the resistive element 22 between the first tubular segment 18 and the second tubular segment 20, the close, frictional fit of the collar tube 21 over the first tubular segment 18 and the second tubular segment 20 may be sufficient, alone, to secure the resistive element 22 between the first tubular segment 18 and the second tubular segment 20.

The distal end 23 of the collar tube 21 is flush with the distal end 25 of the first tubular segment 18, when the collar tube 21 is properly secured over both the first tubular segment 18 and the second tubular segment 20. Additionally, a notch 27, which preferably comprises a punched out semicircle in the distal end 23 of the collar tube 21, is preferably lined up with a port 24 of the second tubular segment. The port 24 of the second tubular segment 20 preferably comprises a punched out circle in the second tubular segment 20. The notch 27 and/or the port 24 may be formed in the collar tube 21 and/or the second tubular segment 20 either before or after assembly of the three pieces 18, 20, and 21. After assembly of the three elements 18, 20, and 21. The port 24 opens directly into a hollow space (FIG. 3) of the air tube 12.

Figure 3:
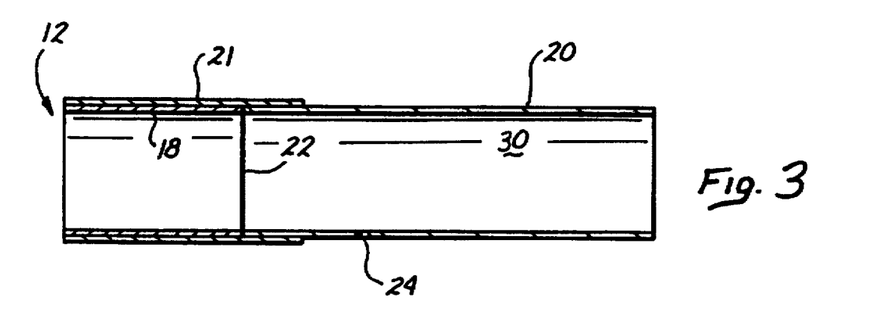
FIG. 3 is a cross-sectional view of the air tube of the presently preferred embodiment.

FIG. 3 illustrates the air tube 12 in an assembled state. Although a three piece configuration of the air tube 12 is presently preferred, these three pieces 18, 20, and 21 may be replaced by a single tube, for example, and/or the resistive element 22 may be secured to an annular ring (not shown), which is inserted within the single tube.

Figures 4, 5:
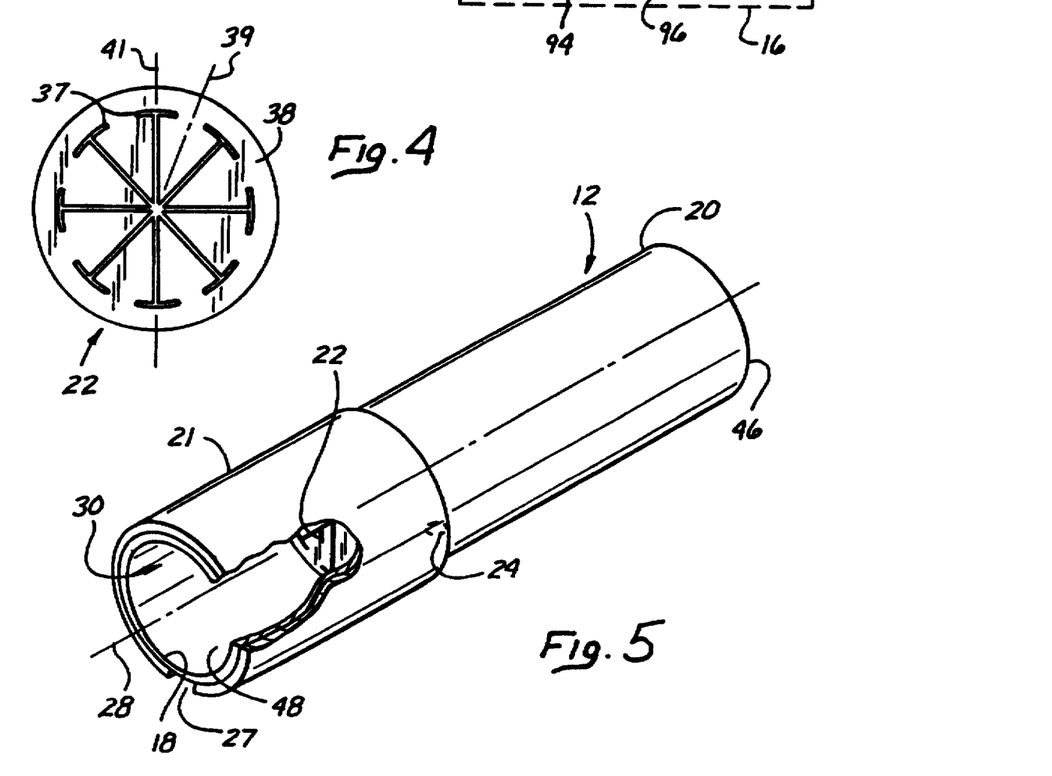
FIG. 4 is a top planar view of the resistive element of the presently preferred embodiment.
FIG. 5 is a partially cut away, top front view, in perspective, of the air tube used in the spirometer shown in FIG. 1.

FIG. 4 illustrates a top planar view of the resistive element 22, according to the presently preferred embodiment. The resistive element 22 comprises a center aperture 32 and a plurality of slots 34 extending radially from the center aperture 32. Each pair of adjacent slots 34 forms a hinged window 36, which as presently embodied comprises an arrowhead shape. Each arrowhead-shaped hinged window 36 comprises a point located near the center aperture 32 and a neck 38 located distally of the center aperture 32. As presently embodied, the resistive element 22 comprises eight hinged windows 36, but greater or fewer numbers of hinged windows 36 may be used according to design parameters. The width of each neck 38 controls the flexibility of the corresponding hinged window 36. A larger neck renders the corresponding hinged window 36 less flexible, and a smaller neck 38 renders the corresponding hinged window 36 more flexible.

A human patient blowing into an end of the air tube 12 at about atmospheric pressure generates an air flow through the resistive element 22 which, typically, may comprises an air flow rate of between zero and 16 liters per second. The resistance provided by the resistive element 22 should, ideally, be approximately linear among these various air flow rates. The alinear flow versus-pressure response of the restistive element 22 is subsequently linearized by software, as presently embodied. Prior art resistive elements, comprising a disk with a single aperture therein, for example, do not have approximately linear pressure versus flow rate relationships. A prior art disk shaped resistive element having a good resistance of less than 1.5 centimeters of water per liter per second at approximately 12 liters per second, for example, will not have a good resistance at lower flow rates. More particularly, such a conventional disk shaped resistive element would have a very low resistance at low flow rates, which is unacceptable.

The resistive element 22 of the present invention utilizes unique hinged windows 36 having necks 38, which can be engineered to tailor the resistance of the resistive element 22 at various flow rates. The resistive element 22 of the present invention is adapted to provide an ideal resistance of less than 1.5 centimeters of water per liter per second at a flow rate of approximately 12 liters per second but, in contrast to a conventional disk shaped resistive element, the resistive element 22 of the present invention also provides good resistance at low flow rates. Generally speaking, the resistive element 22 provides a very good, approximately linear flow-rate-versus-resistance response for flow rates between zero and 16 liters per second. At high flow rates, the hinged windows 36 open widely to provide a good resistance that is not too high. At low flow rates, the hinged windows 36 open very little if any, and air passes through the slots 34 and 37 to thereby provide a good resistance that is not too low.

According to the presently preferred embodiment, an angle between two of the slots 34 is approximately 45 degrees, and each of the slots 34 has a width of approximately 0.02 inches. A preferred width of each of the perpendicular hinged portions 37, which is used to control the width of a neck 38, is approximately 0.04 inches. The diameter of the resistive element 22 is preferably 1.09 inches plus or minus 0.0005 inches, and a width between a line 39 bisecting one of the hinged windows 36, and another line 41 passing through a slot 34 is approximately 0.0625 inches plus or minus 0.005 inches.

One important element of the resistive element 22 of the present invention is the resistance supplied at low flow rates, since, typically, unhealthy patients are unable to generate high flow rates. The same resistive element also functions well at high flow rates. The resistive element 22 provides good resistance at various flow rates, regardless of whether the patient is exhaling or inhaling.

Referring to FIG. 5, air tube 12 includes an open inlet 46 and an open outlet 48. The area surrounding the open inlet 46 is sized and adapted to be fitted into a human being's mouth. This mouthpiece area is employed by the patient using spirometer 10 (FIG. 1) by placing the area 46 into the mouth and exhaling into hollow space 30 of the air tube 12.

Figure 6:
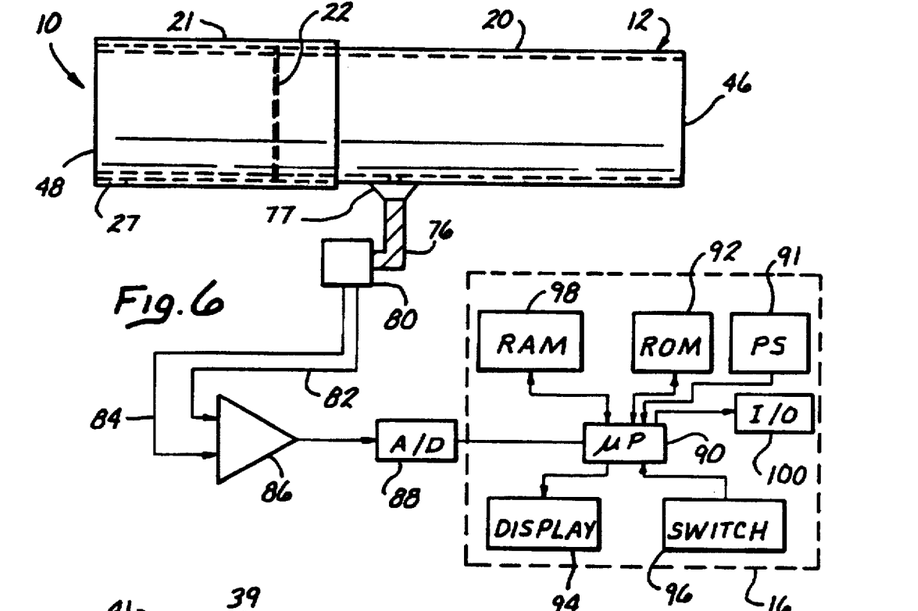
FIG. 6 is a somewhat schematic illustration showing a spirometer in accordance with the present invention.

Turning back to FIG. 1, when it is desired to use air tube 12, it is unpackaged and is coupled to housing 14. In particular, the air tube 12 is coupled to the housing tube 51. The housing tube 51 includes a tab 52, which is adapted to fit within the notch 27 (FIG. 2) of the air tube 12. Before the air tube 12 is placed into the housing tube 51, the notch 27 is aligned with the port 24 (FIG. 2) and, as presently embodied, is manually aligned by the user just before insertion into the housing tube 51. When the notch 27 is aligned with the port 24, the port 24 will align with the pressure sensing leg 76, as shown in FIG. 6. More particularly, a fitting of the pressure sensing leg 76, which preferably comprises a suction cup shape 77 which fits around the port 24 for an airtight fit. The suction cup shaped fitting 77 preferably comprises silicone rubber or vinyl, and is adapted to provide a good fit around the port 24, to thereby attenuate any leakage of air at this interface. Consequently, breath from the patient is not introduced into the pressure sensing leg 76 and contamination of the pressure sensing leg 76 is avoided.

After the notch 27 of the air tube 12 is placed within the housing tube 51 and, more particularly, placed over the alignment tab 52, the distal end 23 of the collar tube 21 should be flush with the distal end of the housing tube 51. At this point, spirometer 10 is ready for use. Note that air tube 12 is longer than housing tube 51 and, when properly coupled to the housing tube, extends beyond one end of the housing tube. The relatively long air tube 12 reduces the risk of air exhaled from the spirometer user coming into effective contact with and contaminating the housing.

FIG. 6 illustrates the general operation of a spirometer, shown generally at 10, in accordance with the present invention. The following is a general description of the operation of the remainder of the spirometer 10 after the air tube 12 is properly located and positioned relative to the pressure sensing leg 76. This general description is applicable using any spirometer, such as spirometer 10, in accordance with the present invention. Through port 24 (FIG. 2) communicates with pressure sensing leg 76. As a further protection against contamination, pressure sensing leg 76 may be equipped with a filter, although this is not required. The pressure sensing leg 76 communicates with a differential pressure transducer 80, which may be, for example, a transducer sold by Motorola under the trademark MPX 2020D. The pressure transducer 80 generates an electrical signal on a pair of output wires 82 and 84, which signal is proportional to the differential pressure between pressure sensing leg 76 and a sensed atmosphere pressure. This signal is amplified by a differential amplifier stage 86 and fed into an analog-to-digital convertor 88 which converts the amplifier output into digital signals.

The output from convertor 88 is fed to a microprocessor 90, which is part of control electronics 16. The microprocessor 90 uses an algorithm stored in a ROM 92 to perform several calculations on the signal from convertor 88, and to display the results, e.g., volume and flow rate, on display 94, for example, a conventional monitor or liquid crystal display module. Microprocessor 90 is powered by a power source 91, for example, a connector capable of being coupled or connected to a source of conventional electric line voltage. Switch 96 can be activated to initiate the operation of the spirometer through microprocessor 90. The results during each measurement may be stored in a RAM 98 for future reference. An input/output port 100 may also be provided to allow for changing the programming of the microprocessor 90. Furthermore, the microprocessor 90 may be programmed so that on command it may download the results accumulated in RAM 98 through input/output port 100 to a printer or a computer.

Waterson et al U.S. Pat. No. 5,137,026 provides further details regarding the operation of such a spirometer. In any event, when a patient has concluded one treatment or diagnostic exercise using the spirometer 10, the biodegradable air tube 12 is removed from the housing tube and is disposed of in an environmentally safe manner.

As shown in FIGS. 1 and 1A, the housing 14 is structured to be gripped in one hand of the user. For example, the shaft 102 of housing 14 is configured for easy hand gripping.

The embodiment shown in FIGS. 1 and 1A includes control electronics 16 located within hand held housing 14. Communication with external computers or printers can occur through cable 106 which can be connected to the convertor using a jack 105, such as a conventional RJ-11 quick connect jack, on housing 14. As presently preferred, communication can also occur through an additional infrared data association (IRDA) link, which is conventional, and operable between the housing 14 and the external computer or printer. Convertor 88, amplifier stage 86 and pressure transducer 80 can be powered through cable 106 from microprocessor 90 and power source 91. Alternatively, the electronics in the housing 14 can be independently powered by a battery pack, such as a conventional rechargeable nickel-cadmium battery. If such a battery pack is used, the housing 14 includes a port through which the battery pack can be charged.

In the embodiment shown in FIGS. 1 and 1A, microprocessor 90 can be a dedicated microprocessor including a transparent-overlay keypad structured and adapted specifically to control the operation of a spirometer. Alternatively, the microprocessor 90 may be a component of a general purpose, personal computer including a full-sized keyboard, video monitor, hard disk drive and printer. The dedicated microprocessor is particularly advantageous because of its relative simplicity, reduced cost and ease of use. In addition, the shaft 102 of housing 14 includes a tapered portion 107, as shown in FIG. 1A, which facilitates placing and maintaining the housing on a flat surface, for example, between uses.

Figure 7:
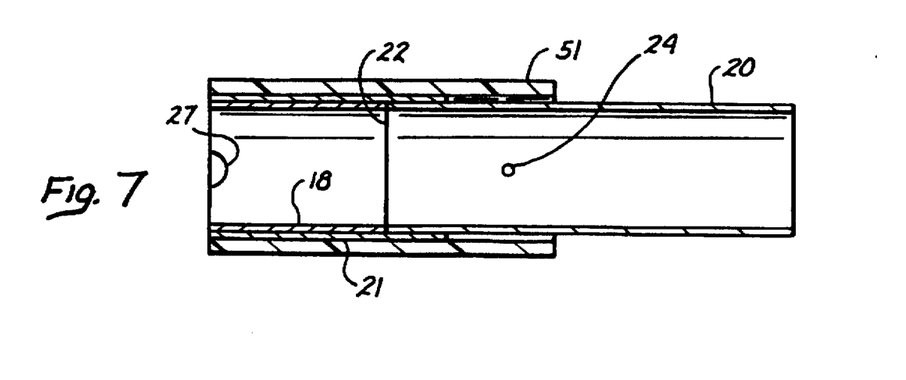
FIG. 7 is a cross-sectional view taken generally along line 7—7 of FIG. 1.

The embodiment shown in FIGS. 1 and 1A is useful as a completely new spirometer, or the air tube 12 and housing 14 can be used to retrofit an existing spirometer. For example, an existing spirometer includes a hand held unit including a permanent breathing tube, pressure sensing leg, a pressure transducer, an amplifier and an analog-to-digital convertor, and is connected to a dedicated control system, which functions in a manner substantially similar to control electronics 16. Simply by replacing the existing hand held unit with housing 14 and the components coupled to or disposed in the housing, a retrofitted spirometer is produced which has many of the advantages of the present invention. FIG. 7 shows a cross-sectional view of the spirometer 10 of FIG. 1, taken along line 7—7 of FIG. 1.

Figure 8:
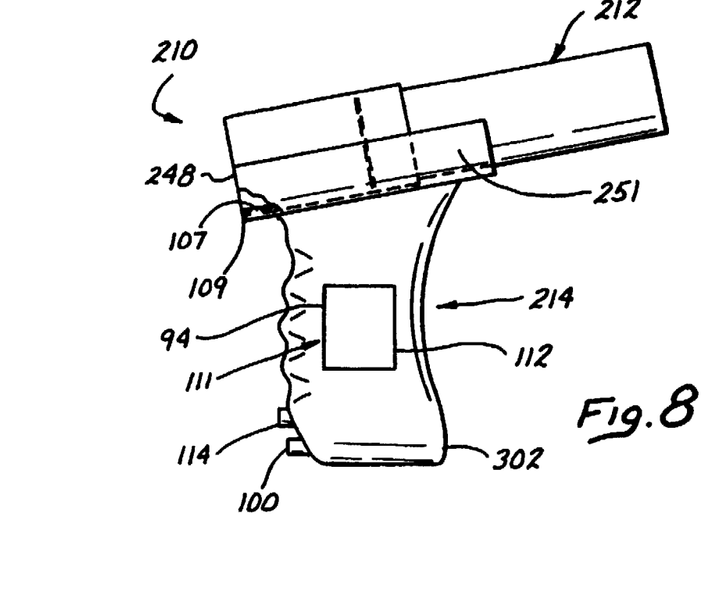
FIG. 8 is a side view of an alternative embodiment of a spirometer in accordance with the present invention.
Figure 9:
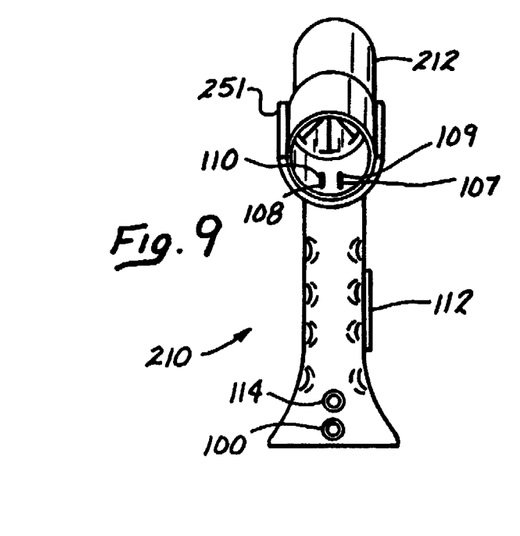
FIG. 9 is a back side view of the spirometer shown in FIG. 8.

Another embodiment of the present invention is illustrated in FIGS. 8 and 9. This spirometer, shown generally at 210, is, except as expressly stated herein, structured in a manner similar to spirometer 10. Components of spirometer 210 which correspond to components of spirometer 10 have corresponding reference numerals increased by 200.

The primary differences between spirometer 210 and spirometer 10 have to do with the configuration of air tube 212 and the configuration of the housing tube 251. Air tube 212 is structured substantially similar to air tube 12 except that in the region near open outlet 248, two positioning ports 107 and 108 are provided.

Housing tube 251 is structured to act as a cradle for air tube 212 rather than surrounding the air tube 212, as does housing tube 51. In addition, housing tube 251 includes two upwardly extending projections 109 and 110 which are positioned to be received by positioning ports 107 and 108, respectively, when air tube 212 is coupled to housing tube 251. With projections 109 and 110 mated to or received by positioning ports 107 and 108, the port 224 (not shown) is properly aligned with the pressure sensing leg 276 (not shown).

As shown in FIGS. 8 and 9, a control transparent-overlay keypad 112 of microprocessor 90 is located on the shaft 302 of housing 214. In addition, this embodiment preferably comprises greater ROM, and the display 94 is located on the housing 214 beneath the transparent-overlay keypad 112. In spirometer 210, the power source 91 is a battery pack, such as a conventional rechargeable nickel-cadmium battery, and is located within housing 214. Port 114 on housing 214 is adapted to provide communication between battery pack 91 and a conventional battery charger to recharge the battery pack when needed. I/O port 100 is also carried by housing 214 and provides convenient communication between microprocessor 90 and a computer or printer, when it is desired to download information from electronic circuitry 111 to such other device. As with the embodiment of FIG. 1, an IRDA optical port is also disposed on shaft 302. Spirometer 210 is a self-contained unit that can be operated by a single patient.

In order to operate spirometer 210, air tube 212 is coupled to housing tube 251 so that projections 109 and 110 mate with positioning ports 107 and 108, respectively. The patient then activates a switch on the transparent-overlay keypad 112 and uses spirometer 210 for any treatment and/or diagnostic procedure desired. When it is desired to remove air tube 212 from housing tube 251, the biodegradable air tube 212 is simply picked up from the housing tube 212 and can be discarded in an environmentally acceptable manner.

Figure 10:
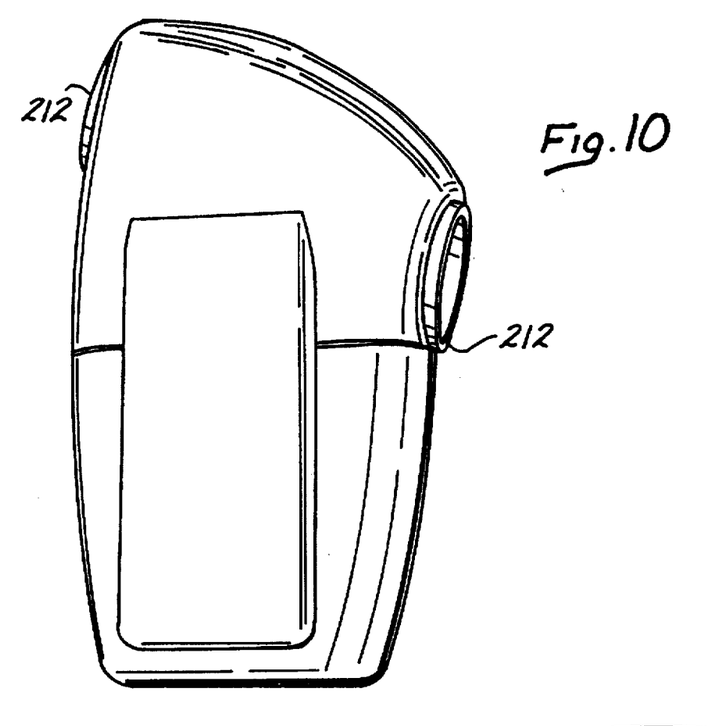
FIGS. 10 and 11 illustrate perspective views of a spirometer design according to the presently preferred embodiment.
Figure 11:
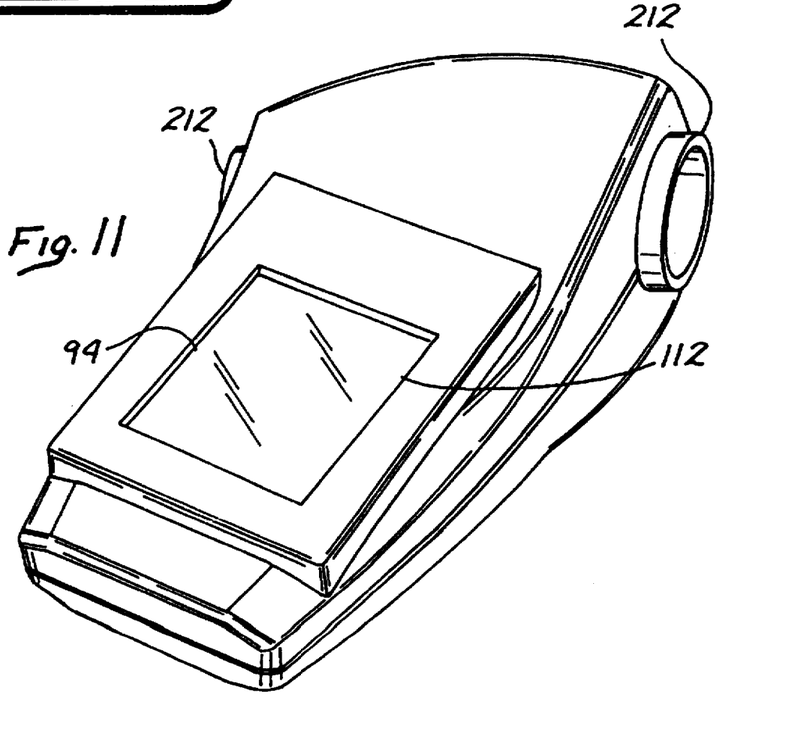

FIGS. 10 and 11 illustrate perspective views of a spirometer design according to the presently preferred embodiment. The air tube 212 is substantially covered by the housing, and the display 94 and transparent-overlay keypad 112 are larger than in previously described embodiments.

While this invention has been described with respect to various specific examples and embodiments, it is to be understood that the invention is not limited thereto and that it can be variously practiced with the scope of the following claims.

What is claimed is:

1. A resistive element for use in a spirometer, comprising:
 a member having a substantially planar first face and an opposing substantially planar second face;
 a plurality of through slots in the member, each of the plurality of through slots having a length and having an inner end and an opposing outer end; and
 a plurality of hinge slots, each of the hinge slots being located at and extending through the outer end of one of the through slots and having a length oriented in a generally different direction relative to the length of the one through slot, the plurality of through slots and the plurality of hinge slots together forming a plurality of hinged windows in the member.

2. The resistive element for use in a spirometer as recited in claim 1, wherein the plurality of through slots and the plurality of hinge slots form at least four hinged windows in the member.

3. The resistive element for use in a spirometer as recited in claim 1, wherein the plurality of through slots and the plurality of hinge slots form at least eight hinged windows in the member.

4. The resistive element for use in a spirometer as recited in claim 1, wherein the number of hinge slots equals the number of through slots.

5. The resistive element for use in a spirometer as recited in claim 1, wherein each hinged window has an arrowhead shape having a point and a generally opposing neck located between two of the hinge slots, the neck having a dimension between the two hinge slots smaller than a similar dimension of the hinged window a distance away from the two hinge slots.

6. The resistive element for use in a spirometer as recited in claim 5, wherein each hinged window is flexible and the dimension of each of the necks controls the flexibility of the corresponding hinged window.

7. The resistive element for use in a spirometer as recited in claim 1, wherein the resistive element has an approximately linear pressure response over a range of air flow rates from zero up to about fifteen liters per second at about atmospheric pressure.

8. A three-piece tube assembly for use in a spirometer, comprising:
 a first tube having a proximal end and a distal end, the first tube having a first outer diameter;
 a second tube having a proximal end and a distal end, the second tube having a second outer diameter that is approximately equal to the first outer diameter;
 a resistive element assembly having uniform thickness located in proximity to the proximal end of the first tube and the distal end of the second tube; and
 a collar tube having a third outer diameter which is larger than the first and second outer diameters, the collar tube surrounding and contacting both the first and second tubes and located at the proximal end of the first tube and the distal end of the second tube.

9. The three-piece tube assembly for use in a spirometer as recited in claim 8, further comprising a port formed in the second tube.

10. The three-piece tube assembly for use in a spirometer as recited in claim 9, further comprising a notch formed in the collar tube.

11. The three-piece tube assembly for use in a spirometer as recited in claim 10, wherein the port is adapted to accommodate a pressure sensing leg of the spirometer, and wherein the notch is adapted to accommodate an alignment tab of the spirometer.

12. The three-piece tube assembly for use in a spirometer as recited in claim 10, wherein the notch is aligned with the port.

13. The three-piece tube assembly for use in a spirometer as recited in claim 12, the port being structured to accommodate a suction-cup shaped member, which is adapted to provide a fluid connection to the pressure sensing leg.

14. The three-piece tube assembly for use in a spirometer as recited in claim 8, wherein the resistive element is bonded to at least one of the first tube and the second tube.

15. A resistive element for use in a spirometer, comprising:
 a thin, disk shaped, resilient membrane;
 a plurality of through slots in the membrane at least in part forming a plurality of spaced apart in an undefelcted state, hinged windows in the membrane; and
 the resistive element being adapted to provide a resistance which has an approximately linear pressure response over a range of air flow rates from zero up to about 15 liters per second at about atmospheric pressure.

16. The resistive element for use in a spirometer as recited in claim 15, wherein the plurality of through slots provides a first predetermined resistance to low air flow rates through the resistive element, and the plurality of spaced apart hinged windows provides a second predetermined resistance to high air flow rates through the resistive element.

17. The resistive element for use in a spirometer as recited in claim 15, which resistive element provides a resistance of less than approximately 1.5 centimeters of water per liter per second at an air flow rate of 12 liters per second at about atmospheric pressure.

18. The resistive element for use in a spirometer as recited in claim 15, wherein the resistance provided by the resistive element at an air flow rate of 3 liters per second at about atmospheric pressure is substantially greater than the resistance of a similarly sized resistive element comprising only a disk and a large aperture.

19. The resistive element for use in a spirometer as recited in claim 15, wherein the plurality of spaced apart hinged windows are adapted to open slightly at low flow rates and to open to a substantially greater extent at high flow rates.

20. The resistive element for use in a spirometer as recited in claim 15, wherein the plurality of through slots at least in part forms at least four spaced apart hinged windows in the member.

21. A three-piece tube assembly for use in a spirometer, comprising;

a first tube having a proximal end and a distal end, the first tube having a first outer diameter;

a second tube having a proximal end and a distal end, the second tube having a second outer diameter that is approximately equal to the first outer diameter;

a resistive element having a substantially uniform thickness and being located in proximity to the proximal end of the first tube and the distal end of the second tube; and a collar tube having a third outer diameter which is larger than the first and second outer diameters, the collar tube being coupled to both the first and second tubes and located over both the proximal end of the first tube and the distal end of the second tube.

* * * * *